United States Patent
Gallucci et al.

(10) Patent No.: US 10,434,705 B2
(45) Date of Patent: Oct. 8, 2019

(54) ADDITIVE MANUFACTURED ITEMS WITH FLAME RESISTANCE, PROCESS FOR MAKING AND PROCESS FOR TESTING THEIR FLAME PERFORMANCE

(71) Applicant: SABIC Global Technologies B.V., Bergen op Zoom (NL)

(72) Inventors: Robert Russell Gallucci, Mt. Vernon, IN (US); Thomas Hocker, Pittsfield, MA (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 393 days.

(21) Appl. No.: 15/123,379

(22) PCT Filed: Feb. 27, 2015

(86) PCT No.: PCT/US2015/017967
§ 371 (c)(1),
(2) Date: Sep. 2, 2016

(87) PCT Pub. No.: WO2015/134316
PCT Pub. Date: Sep. 11, 2015

(65) Prior Publication Data
US 2017/0072631 A1      Mar. 16, 2017

Related U.S. Application Data

(60) Provisional application No. 61/948,807, filed on Mar. 6, 2014.

(51) Int. Cl.
*B29C 64/118* (2017.01)
*B33Y 10/00* (2015.01)
(Continued)

(52) U.S. Cl.
CPC .......... *B29C 64/118* (2017.08); *B29C 64/106* (2017.08); *B33Y 10/00* (2014.12);
(Continued)

(58) Field of Classification Search
CPC ..... B29C 64/10; B29C 64/106; B29C 64/118; B29C 64/188; B29C 64/232;
(Continued)

(56) References Cited

U.S. PATENT DOCUMENTS

| 2,999,835 A | 9/1961 | Goldberg |
| 3,153,008 A | 10/1964 | Fox |

(Continued)

FOREIGN PATENT DOCUMENTS

WO    2015077053 A1    5/2015

OTHER PUBLICATIONS

"Aircraft Materials Fire Test Handbook" DOT/FAA/AR-00/12, Chapter 5 "Heat Release Test for Cabin Materials"; 2000; 20 pages.
(Continued)

*Primary Examiner* — Seyed Masoud Malekzadeh
*Assistant Examiner* — Taryn Trace Willett
(74) *Attorney, Agent, or Firm* — Cantor Colburn LLP

(57) ABSTRACT

A process for making an article by additive manufacture having resistance to dripping when burned comprising (1) depositing a multitude of thermoplastic monofilament strands using a fused deposition modeling apparatus in a pattern and (2) fusing the multitude of strands together to make an article of manufacture having voids therein; wherein the article of additive manufacture has (a) at least 50% of the monofilament strands oriented within 45 degrees of the long part of the axis; (b) the multitude of strands is greater than 10; (c) having a specific micro structure; and (d) is made from a thermoplastic polymer composition that is either the combination of a thermoplastic polymer with a
(Continued)

flame retardant compound, a thermoplastic resin having flame resistant properties, or a combination of a thermoplastic resin having flame resistant properties with a flame retardant compound.

16 Claims, 4 Drawing Sheets

(51) Int. Cl.
| | |
|---|---|
| B33Y 40/00 | (2015.01) |
| B33Y 70/00 | (2015.01) |
| B33Y 80/00 | (2015.01) |
| G01N 33/44 | (2006.01) |
| B29C 64/106 | (2017.01) |
| B29K 105/00 | (2006.01) |

(52) U.S. Cl.
CPC .............. *B33Y 40/00* (2014.12); *B33Y 70/00* (2014.12); *B33Y 80/00* (2014.12); *G01N 33/442* (2013.01); *B29K 2105/0026* (2013.01); *B29K 2995/0016* (2013.01)

(58) Field of Classification Search
CPC ..... B29C 64/236; B29C 64/241; B33Y 80/00; B33Y 70/00; B33Y 40/00; B33Y 10/00; B29K 2995/0016; B29K 2105/0026; G01N 33/442
See application file for complete search history.

(56) References Cited

U.S. PATENT DOCUMENTS

| | | | |
|---|---|---|---|
| 3,334,154 A | | 8/1967 | Kim |
| 4,001,184 A | | 1/1977 | Scott |
| 4,123,436 A | | 10/1978 | Holub et al. |
| 4,131,575 A | | 12/1978 | Adelmann et al. |
| 4,636,544 A | | 1/1987 | Hepp |
| 5,034,458 A | | 7/1991 | Serini et al. |
| 5,387,639 A | | 2/1995 | Sybert et al. |
| 5,521,230 A | | 5/1996 | Bhatia et al. |
| 5,672,645 A | | 9/1997 | Eckel et al. |
| 5,674,802 A | * | 10/1997 | Sheppard ................. B01J 19/30 502/439 |
| 5,863,974 A | | 1/1999 | Tjahjadi et al. |
| 5,866,058 A | | 2/1999 | Batchelder et al. |
| 5,968,561 A | | 10/1999 | Batchelder et al. |
| 6,255,371 B1 | | 7/2001 | Schlosser et al. |
| 6,256,146 B1 | * | 7/2001 | Merrill ................. G02B 5/3008 252/585 |
| 6,605,657 B1 | | 8/2003 | Favis et al. |
| 6,605,659 B2 | | 8/2003 | Blackburn et al. |
| 6,609,043 B1 | | 8/2003 | Zoia et al. |
| 7,452,944 B2 | | 11/2008 | Gallucci et al. |
| 7,652,107 B2 | | 1/2010 | Gallucci et al. |
| 7,790,292 B2 | | 9/2010 | Colborn et al. |
| 7,812,077 B2 | | 10/2010 | Borade et al. |
| 7,932,310 B2 | | 4/2011 | Gallucci et al. |
| 8,017,699 B1 | | 9/2011 | Sanner et al. |
| 8,236,227 B2 | | 8/2012 | Batchelder et al. |
| 8,263,691 B2 | | 9/2012 | Gallucci et al. |
| 8,292,610 B2 | | 10/2012 | Hehl |
| 8,309,637 B2 | | 11/2012 | Sanner et al. |
| 8,349,933 B2 | * | 1/2013 | Bhandari ............. C08G 73/106 524/422 |
| 9,011,982 B2 | | 4/2015 | Muller et al. |
| 9,283,714 B2 | | 3/2016 | Pridoehl et al. |
| 2002/0113331 A1 | * | 8/2002 | Zhang ................. B29C 41/003 264/40.1 |
| 2002/0137827 A1 | | 9/2002 | Tomioka et al. |
| 2004/0099996 A1 | * | 5/2004 | Herzog ................. B22F 3/1055 264/401 |
| 2005/0154099 A1 | * | 7/2005 | Kobayashi .......... B29C 66/7394 524/99 |
| 2005/0242473 A1 | * | 11/2005 | Newell ................. B29C 64/153 264/497 |
| 2005/0288813 A1 | * | 12/2005 | Yang ..................... B22F 3/1055 700/119 |
| 2007/0036964 A1 | * | 2/2007 | Rosenberger ........... B32B 27/08 428/304.4 |
| 2007/0179657 A1 | * | 8/2007 | Holzwarth ............. B33Y 50/02 700/119 |
| 2007/0290410 A1 | * | 12/2007 | Koo ..................... B29C 64/153 264/497 |
| 2008/0153947 A1 | * | 6/2008 | Booth ................... B29C 64/153 524/81 |
| 2008/0241392 A1 | * | 10/2008 | Dimter ................. B22F 3/1055 427/256 |
| 2009/0062436 A1 | * | 3/2009 | Breiner ................. C08K 5/523 524/117 |
| 2010/0171241 A1 | * | 7/2010 | Huskamp ............... B33Y 10/00 264/497 |
| 2010/0233474 A1 | * | 9/2010 | Haruhara ............ B29C 65/1635 428/339 |
| 2011/0071241 A1 | * | 3/2011 | Rogunova ............. C08K 5/109 524/127 |
| 2012/0251750 A1 | * | 10/2012 | Sybert .................... C08L 83/10 428/35.7 |
| 2012/0252961 A1 | | 10/2012 | Sybert et al. |
| 2013/0071599 A1 | * | 3/2013 | Kraibuhler ............ B29C 64/112 428/57 |
| 2013/0224461 A1 | | 8/2013 | Van Der Mee et al. |
| 2013/0261202 A1 | | 10/2013 | Cao et al. |
| 2013/0284991 A1 | | 10/2013 | Sybert et al. |
| 2014/0080973 A1 | * | 3/2014 | Alberts ...................... C08J 5/24 524/878 |
| 2015/0197060 A1 | * | 7/2015 | Carr .................... B29C 67/0055 264/40.1 |
| 2016/0159007 A1 | * | 6/2016 | Miller, IV ............ D21F 1/0027 162/348 |
| 2017/0058175 A1 | * | 3/2017 | Gasworth ............. C09K 5/063 |
| 2017/0368758 A1 | * | 12/2017 | Touma .................. B33Y 30/00 |
| 2018/0071979 A1 | * | 3/2018 | Achten ................. B33Y 10/00 |
| 2018/0147773 A1 | * | 5/2018 | Kalyanaraman ... C08G 73/1028 |

OTHER PUBLICATIONS

Comb et al.; "Layered Manufacturing Control Parameters and Material Selection Criteria"; Manufacturing Science and Engineering, vol. 2; 1994; pp. 547-556.
El-Gizawy et al.; "An integrated approach for characterization of properties and mesostructure of fused deposition modeling ULTEM 9085 products"; Database Compendex, Database Accession No. E20104813443888 Abstract; 2010; 1 page.
International Preliminary Report for international Application No. PCT/US2015/017967; International Filing Date Feb. 27, 2015; dated Sep. 15, 2016; 6 pages.
International Preliminary Report on Patentability for International Application No. PCT/US2014/064558; International Filing Date Nov. 7, 2014; dated May 24, 2016; 7 pages.
International Search Report for International Application No. PCT/US2014/064558; International Filing Date Nov. 7, 2014; dated Apr. 21, 2015; 6 pages.
International Search Report for International Application No. PCT/US2015/017967; International Filing Date Feb. 27, 2015; dated May 13, 2015; 4 pages.
Masood et al.; "Tensile Properties of Processed FDM Polycarbonate Material"; Materials Science Forum, vols. 654-656; 2010; pp. 2556-2559.
Novakova-Marcincinova et al.; "Special Materials Used in FDM Rapid Prototyping Technology Application"; IEEE 16th International Conference on Intelligent Engineering Systems; 2012; pp. 73-76.
Rodriguez et al.; "Characterization of the mesostructure of fused-deposition acrylonitrile-butadiene-styrene materials"; Rapid Prototyping Journal, vol. 6, No. 3; 2000; pp. 175-185.
Wohlers; "Making Products by Using Additive Manufacturing"; 2011; pp. 70-77; Retrieved from http://www.sme.org/uploadedFiles/Publications/ME_Magazine/2011/April_2011/April%202011%20f1%20Additive.pdf.

(56) References Cited

OTHER PUBLICATIONS

Written Opinion for International Application No. PCT/US2014/064558; International Filing Date Nov. 7, 2014; dated Apr. 21, 2015; 7 pages.
Written Opinion for International Application No. PCT/US2015/017967; International Filing Date Feb. 27, 2015; dated May 13, 2015; 5 pages.
Ziemian et al.; "Anisotropic Mechanical Properties of ABS Parts Fabricated by Fused Deposition Modelling"; Mechanical Engineering, Dr. Murat Gokcek (Ed.); 2012; pp. 159-181.
Ei-Gizawy A S; Cardona J; Graybill B: International SAMPE Symposium and Exhibition (Proceedings)—SAMPE 2010 Conference and Exhibition "New Materials and Processes for a New Economy" 2010 Soc. For the Advancement of Material and Process Engineering USA, May 17, 2010-May 20, 2010.
China Office Action for Chinese Patent Application No. 2014800639935; dated Mar. 3, 2017; 3 pages; Non-English Translation.
China Office Action for Chinese Patent Application No. 2014800639935; dated Mar. 3, 2017; 7 pages; English Translation.

* cited by examiner

ADDITIVE MANUFACTURED ITEMS WITH FLAME RESISTANCE, PROCESS FOR MAKING AND PROCESS FOR TESTING THEIR FLAME PERFORMANCE

CROSS REFERENCE TO RELATED APPLICATIONS

This application is a National Stage application of PCT/US2015/017967, filed Feb. 27, 2015, which claims the benefit of U.S. Provisional Application No. 61/948,807, filed Mar. 6, 2014, both of which are incorporated by reference in their entirety herein.

BACKGROUND

Additive Manufacturing (AM) is a production technology that is transforming the way all sorts of things are made. AM makes three-dimensional (3D) solid objects of virtually any shape from a digital model. Generally, this is achieved by creating a digital blueprint of a desired solid object with computer-aided design (CAD) modeling software and then slicing that virtual blueprint into very small digital cross-sections. These cross-sections are formed or deposited in a sequential layering process in an AM machine to create the 3D object. AM has many advantages, including dramatically reducing the time from design to prototyping to commercial product. Running design changes are possible. Multiple parts can be built in a single assembly. No tooling is required. Minimal energy is needed to make these 3D solid objects. It also decreases the amount waste and raw materials. AM also facilitates production of extremely complex geometrical parts. AM also reduces the parts inventory for a business since parts can be quickly made on-demand and on-site. However, there is a need for making AM parts that are resistant to ignition and especially to flame. In particular, there is a need for AM parts to have a V-0 rating with the UL-94 FR vertical burn test. Conventional AM parts made by a monofilament additive manufacturing technique (for example, fused deposition modeling (FDM) or fused filament fabrication (FFF) process) are made from a large series of monofilament strands that are from 0.1 to 3.0 mm in diameter. These strands rely on contact with each other in an oven at atmospheric pressure to bond with each other; this results in AM parts having a very high degree of interaction between strand surfaces with a small portion voids in those bonded strands. It has been found that unlike standard injection molded parts, these conventional AM parts are not fully packed and the resulting monofilament strand interfaces are a weak link that makes the AM parts more prone to dripping during the UL-94 test. In particular, the AM parts can begin to melt and separate at the strand interface in the UL-94 test, which can cause dripping and creates a dangerous situation where fire can spread. Thus, there is a need to overcome this problem.

BRIEF DESCRIPTION

One embodiment can be a process for making an article by additive manufacturing having a resistance to dripping when burned comprising (1) depositing a multitude of thermoplastic monofilament strands each having a diameter from 0.1 to 20.0 mm using a fused deposition modeling apparatus in a pattern and (2) fusing the multitude of strands together to make an article of manufacture having voids therein; wherein the article of additive manufacture comprises a thermoplastic polymer composition, the article of manufacture having (a) at least 50% of the monofilament strands oriented within 45 degrees of the long part of the axis; (b) the multitude of strands is greater than 10; (c) a micro structure as measured by optical microscopy containing from 1% to 20% by volume of voids wherein at least 80% of the voids are high aspect voids and less than 20% of the voids are spherical voids with a diameter of 10 to 100 microns; and (d) wherein the thermoplastic polymer composition comprises either the combination of a thermoplastic polymer with a flame retardant compound, a thermoplastic polymer having flame resistant properties, or a combination of a thermoplastic polymer having flame resistant properties with a flame retardant compound.

Another embodiment can be a reduced density article of manufacture made by the above process wherein at least 90% of the voids are high aspect voids and less than 10% of the voids are spherical voids with a diameter of 10 to 100 microns.

Another embodiment can be an article made by additive manufacturing having a resistance to dripping when burned comprising a thermoplastic polymer composition, the article of manufacture having (a) at least 50% of the monofilament strands oriented within 45 degrees of the long part of the axis; (b) the multitude of strands is greater than 10; (c) a micro structure as measured by optical microscopy containing from 1% to 20% by volume of voids wherein at least 80% of the voids are high aspect voids and less than 20% of the voids are spherical voids with a diameter of 10 to 100 microns; and (d) wherein the thermoplastic polymer comprises is either the combination of a thermoplastic polymer with a flame retardant compound (sometimes referred to herein as a FR), a thermoplastic polymer having flame resistant properties, or a combination thermoplastic polymer having flame resistant properties with a flame retardant compound.

Still another embodiment can be process for testing the UL-94 flame performance of an article of additive manufacture comprising the steps of: (1) forming a monofilament additive manufactured rectangular part with a width of 0.5 to 2.5 centimeters, a length of at least 10 centimeters, and a thickness of 0.1 to 10 millimeters from a multitude of thermoplastic monofilament strands having a diameter from 0.1 to 20.0 mm using a fused deposition modeling apparatus; the part having (a) at least 50% of the monofilament strands oriented within 45 degrees of the long axis of the part; (b) the multitude of strands is greater than 10; (c) a micro structure as measured by optical microscopy containing from 1% to 20% by volume of voids wherein at least 80% of the voids are high aspect voids and less than 20% of the voids are spherical voids with a diameter of 10 to 100 microns; and (d) wherein the thermoplastic polymer comprises is either a thermoplastic polymer having flame resistant properties, the combination of a thermoplastic polymer with a flame retardant compound, or a combination thermoplastic polymer having flame resistant properties with a flame retardant compound; (2) equilibrating the formed part for at least 24 hours at 50% relative humidity and at 20 to 25 degrees C.; (3) clamping the part so that the long axis of the part is in a vertical position located 5 inches above a dry cotton piece; (4) applying a flame to the long axis of the part two times, each flame application being 10 seconds in duration; and (5) observing that no dripping from the part occurs that is sufficient to ignite the dry cotton piece.

The above described and other features are exemplified by the following figures and detailed description.

Figure 1:
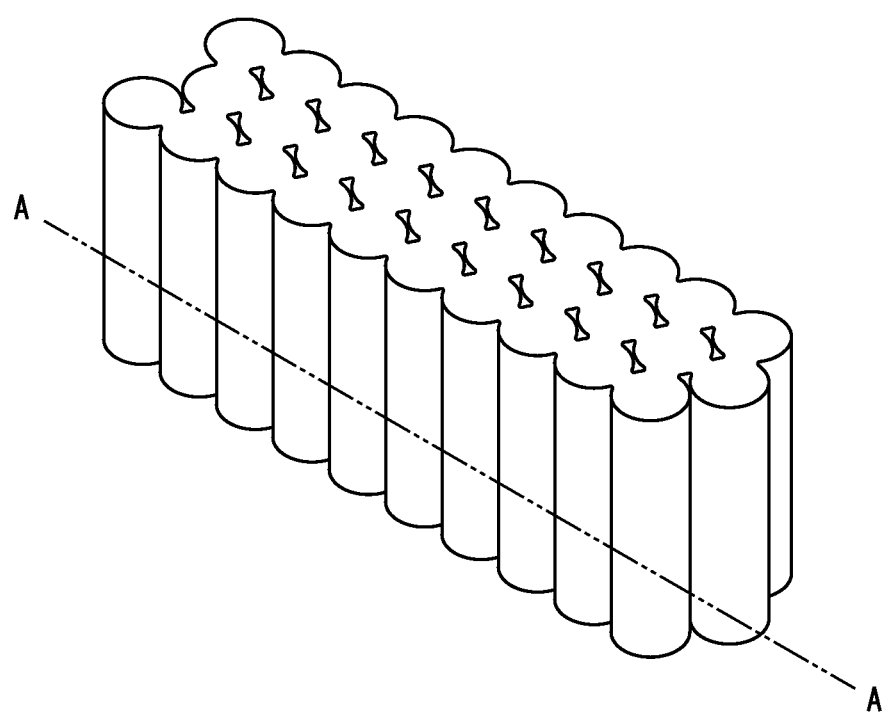
FIG. 1 represents a schematic representation of a portion of a part made by extruding monofilaments in a 90×90 degree orientation. The A-A line represents the long axis of the part. This representation is not a fully faithfully reduction of all of the details of a part made in this orientation.
Figure 2:
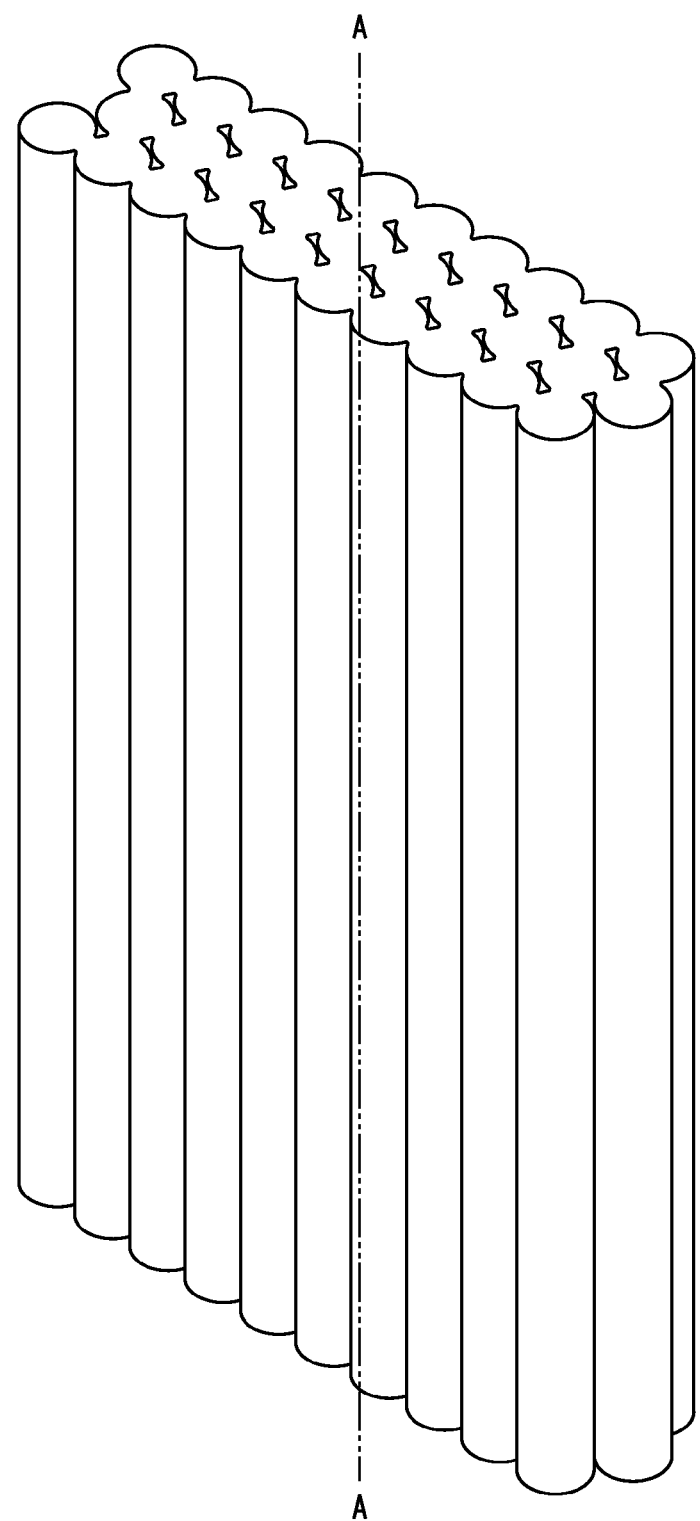

FIG. 2 represents a schematic representation of a portion of a part made by extruding monofilaments in a 0×0 degree orientation. The A-A line represents the long axis of the part. This representation is not a fully faithfully reduction of all of the details of a part made in this orientation.

Figure 3:
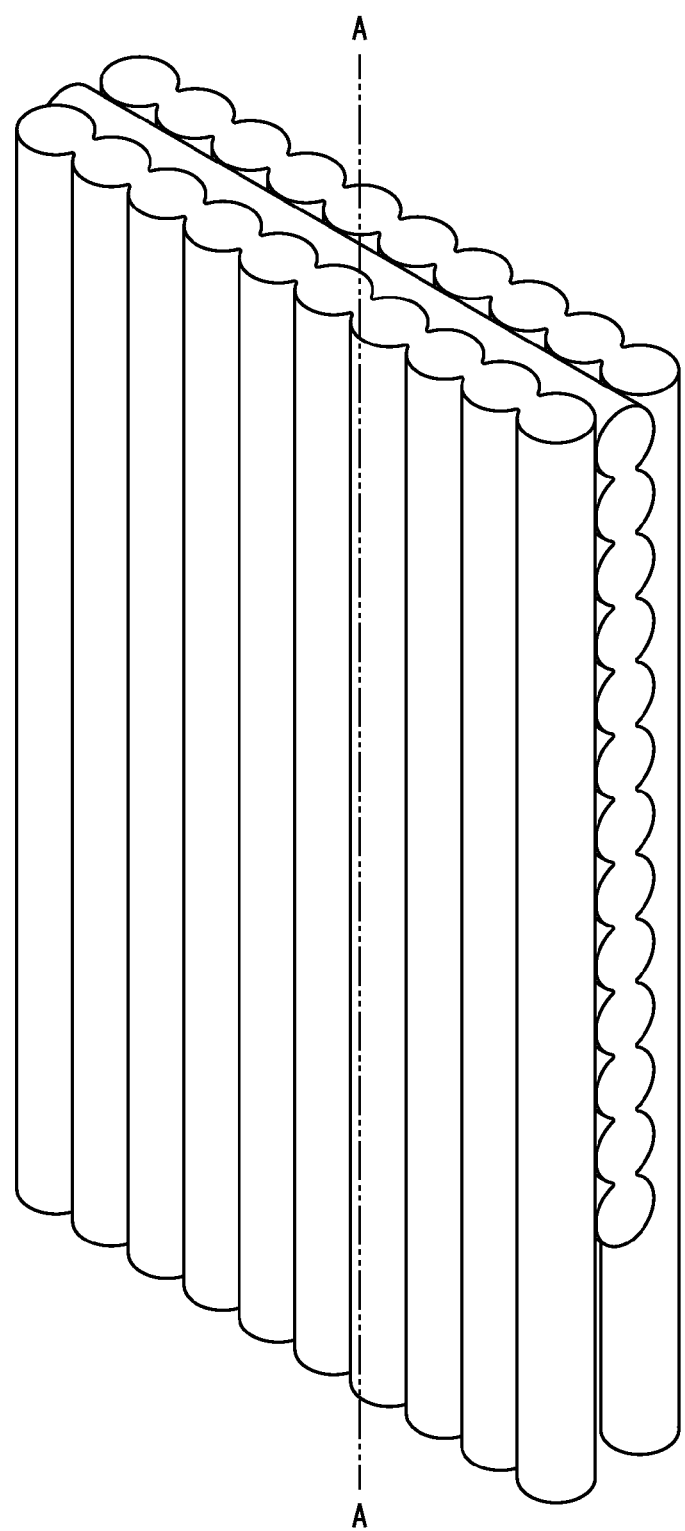

FIG. 3 represents a schematic representation of a portion of a part made by extruding monofilaments in a 0×90 degree orientation. The A-A line represents the long axis of the part. This representation is not a fully faithfully reduction of all of the details of a part made in this orientation.

Figure 4:
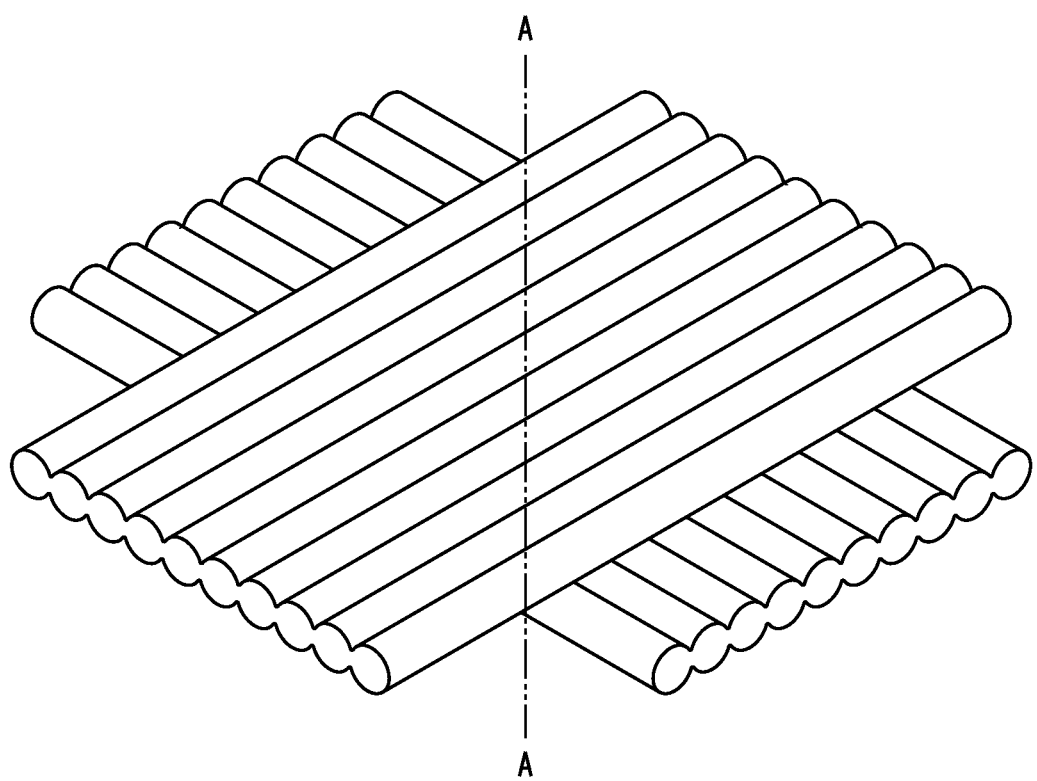

FIG. 4 represents a schematic representation of a portion of a part made by extruding monofilaments in a 45×135 degree orientation. The A-A line represents the long axis of the part. This representation is not a fully faithfully reduction of all of the details of a part made in this orientation.

DETAILED DESCRIPTION

These AM articles of manufacture have the advantage of improved resistance to dripping when burned under either UL-5VB or UL-94 testing, for example, passing the latter test with higher ratings, for example V-1 or V-2. This is the result of the combination of using specific depositing parameters with particular voided areas in the micro-structure of those articles along with the physical properties of the specific thermoplastic compositions used to make that build. Also, the design flexibility and facile changes to part geometry of the monofilament AM process are still retained in these AM articles of manufacture.

The term "reduced density" as used in the present specification and claims means that the article of manufacture will have a density that is less than similar shaped article of manufacture having no voids made by a standard injection molding process of that same material. In addition, reduced density articles herein have a high percentage of high aspect voids and a low percentage of spherical voids therein.

The term "monofilament additive manufacturing technique" as used in the present specification and claims means that the article of manufacture can be made by any additive manufacturing technique that makes a three-dimensional solid object of any shape by laying down material in layers from a plastic monofilament from a digital model. For example, the monofilament can be made by laying down a plastic filament that is unwound from a coil or is deposited from an extrusion head. These monofilament additive manufacturing techniques include fused deposition modeling (FDM) and fused filament fabrication (FFF).

The term "aspect ratio" as used on this specification and claims means the ratio of longest or major length of the void to the shortest or minor length of the void.

The term "high aspect voids" as used in the present specification and claims means that the means the aspect ratio of the void is greater than 2:1. One optional type of high aspect voids can be angular voids having a cusp angle that is an acute angle of 60 degrees or less. These angular voids can be optionally present in amounts at least 20% of the voids.

The term "spherical voids" as used in the present specification and claims means that the aspect ratio of the void is less than 1.5:1.

The terms "Fused Deposition Modeling (FDM)" or "Fused Filament Fabrication (FFF)" involves building a part or article layer-by-layer by heating thermoplastic material to a semi-liquid state and extruding it according to computer-controlled paths. FDM utilizes a modeling material and a support material. The modeling material comprises the finished piece, and the support material comprises scaffolding that can be mechanically removed, washed away or dissolved when the process is complete. The process involves depositing material to complete each layer before the base moves down the Z-axis and the next layer begins.

The term "polycarbonate" as used herein means a polymer or copolymer having repeating structural carbonate units of formula (1)

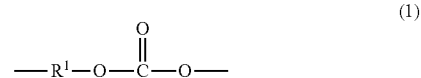

(1)

wherein at least 60 percent of the total number of R1 groups are aromatic, or each R1 contains at least one C6-30 aromatic group. Specifically, each R1 can be derived from a dihydroxy compound such as an aromatic dihydroxy compound of formula (2) or a bisphenol of formula (3):

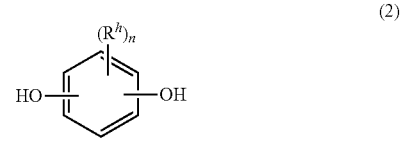

(2)

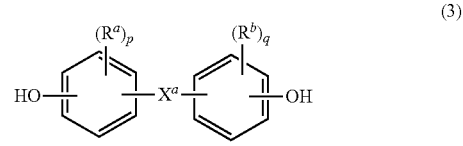

(3)

In formula (2), each Rh is independently a halogen atom, for example bromine, a C1-10 hydrocarbyl group such as a C1-10 alkyl, a halogen-substituted C1-10 alkyl, a C6-10 aryl, or a halogen-substituted C6-10 aryl, and n is 0 to 4. The aromatic polycarbonates can be manufactured by any processes such as by reacting a dihydric phenol with a carbonate precursor, such as phosgene, a haloformate or carbonate ester in melt or solution. U.S. Pat. No. 4,123,436 describes reaction with phosgene and U.S. Pat. No. 3,153,008 describes a transesterification process. The dihydric phenols employed to provide such aromatic carbonate polymers may be mononuclear or polynuclear aromatic compounds, containing as functional groups two hydroxy radicals, each of which is attached directly to a carbon atom of an aromatic nucleus. Typical dihydric phenols include, for example, 2,2-bis(4-hydroxyphenyl)propane (bisphenol A); hydroquinone; resorcinol; 2,2-bis(4-hydroxyphenyl)pentane; 2,4'-(dihydroxydiphenyl)methane; bis(2-hydroxyphenyl)methane; bis(4-hydroxyphenyl)methane; bis(4-hydroxy-5-nitrophenyl)methane; 1,1-bis(4-hydroxyphenyl)ethane; 3,3-bis(4-hydroxyphenyl)pentane; 2,2-dihydroxydiphenyl; 2,6-dihydroxynaphthalene; bis(4-hydroxydiphenyl)sulfone; bis(3,5-diethyl-4-hydroxyphenyl)sulfone; 2,2-bis(3,5-dimethyl-4-hydroxyphenyl)propane; 2,4'-dihydroxydiphenyl sulfone; 5'-chloro-2,4'-dihydroxydiphenyl sulfone; bis(4-hydroxyphenyl)diphenyl sulfone; 4,4'-dihydroxydiphenyl ether; 4,4'-dihydroxy-3,3'-dichlorodiphenyl ether; 4,4-dihydroxy-2,5-dihydroxydiphenyl ether; and the like. Other dihydric phenols suitable for use in the preparation of polycarbonate resins are described, for example, in U.S. Pat. No. 2,999,835 to Goldberg, U.S. Pat. No. 3,334,154 to Kim, U.S. Pat. No.

4,131,575 to Adelmann et al. and U.S. Pat. No. 5,034,458 to Serini et al. Polycarbonates may be branched or linear and generally will have a weight average molecular weight of about 10,000 to about 200,000, preferably from about 20,000 to about 100,000 as measured by gel permeation chromatography. The polycarbonates of the invention can employ a variety of end groups to improve performance. Bulky monophenols, such as cumyl phenol, are preferred. The polycarbonates can be made by any method of Polymerization, for example interfacial or melt polymerization.

The monofilament manufactured articles can be formed by (1) depositing a multitude of thermoplastic monofilaments using a fused deposition modeling apparatus in a particular layer or crossing pattern and then (2) fusing the multitude of strands together with heat to make article of manufacture having improved resistance to dripping Often the article will have from 10 to 10,000 monofilament layers of varying orientation and placement, making a wide variety of shapes of varying dimensions and thicknesses. In some instances, the shape will be hollow with a wall thickness from 1 to 30 mm. In those instances, the voids described herein will be found in the walls of the article. The monofilaments can have a diameter from 0.01 to 5.0 mm. The monofilament can be made by any known technique, for example, melt extrusion through a forming die of polymer pellets or granules.

In this process for making an article by additive manufacturing having a resistance to dripping when burned, the step of depositing the multitude of thermoplastic monofilament strands each having a diameter from 0.1 to 20.0 mm using a fused deposition modeling apparatus in a pattern can occur in several different ways as long as at least 50% of the monofilament strands are oriented within 45 degrees of the long part of the axis (or the length of the part). The depositing can occur where the layers of monofilament strands are deposited upon each lengthwise with no crossing at all (0×0); or wherein the monofilaments of alternating layers cross each other at an angle of from 60 to 120 degrees; or wherein the monofilaments of alternating layers cross each other at an angle of from 85 to 95 degrees. In one embodiment, the monofilaments of alternating layers cross each other at an angle of from 60 to 120 degrees and at least half of said monofilaments are oriented from 0.1 to 45 degrees, in some instances 1.0 to 45 degrees, of the longest axis of the part. In other embodiment, the monofilaments of alternating layers cross each other at an angle of from 60 to 120 degrees and at least half of said monofilaments are parallel to the longest axis of the part.

The fusing step is carried out by heating the stacked stands together to for an integral AM part. In some instance monofilament consolidation into an anti-drip AM part can be achieved at 120 to 250 degrees C. In other instances, monofilament processing can occur from at an oven setting from 120 to 180 degrees C. In yet other instances the consolidation of the monofilament consolidation will occur at or near the glass transition temperature (Tg) of the resin, for example within 10 degrees C. of the Tg. Depending on the resin and part design higher temperatures, for example 20 to 100 degrees C. above the Tg may be employed. Very high temperature may need to be avoided as the consolidated anti-drip AM part may sag or lose shape. "Very high temperatures" will vary with the Tg of the resin and can be determined during the manufacture of the AM part or device by those skilled in the art. In some instances 150 degrees C. above the Tg will gave a thermoplastic resin that is too fluid for AM part manufacture. The Tg of a resin may be measured as per ASTM D7426 at a heating rate of 10 degrees C./min. The time to build AM parts can vary widely depending on the size and complexity of the part, sometimes ranging from an hour to 8 hours or more. In some instances several parts will be made at the same time. The heating rate and temperature used for AM part consolidation can be optimized by those skilled in the art to balance part quality with the speed of part build. In many instances the desired anti-drip AM part will be made simultaneously with a support structure. The support structure may later (after cooling) be removed by mechanical of chemical means. In some instances the support structure will comprise a water soluble resin. If the support structure is thermoplastic material, it may be recovered and recycled for later use. In some instances, the fusing of the monofilament strands can be carried out by heating of the monofilament in an inert atmosphere containing less than 1 volume % oxygen. The inert atmosphere may be chosen from nitrogen, carbon dioxide, argon, krypton. and xenon and mixtures thereof. Use of a non-oxidizing atmosphere can protect the monofilament manufactured article from oxidative degradation. Degradation can manifest itself in many ways, for instance a change in color. In other instances degradation results in a loss of impact. This is especially true in blends of polycarbonate with rubber for example unsaturated butadiene based rubbery polymers such as MBS and ABS. A non-oxidizing atmosphere can also help to prevent the degradation of stabilizers in the monofilament manufactured process (MMP) so that there is still some stabilizer remaining after forming in order to protect the article in its final use. Examples of stabilizers that would otherwise be consumed in an oxidizing monofilament forming process include; hindered phenols, thioesters, phosphites and combinations thereof. The long fusing time needed to form additive manufactured articles places the resin at high temperature, near or above the glass transition (Tg) temperature for greater than 2 hours and in some instances greater than 4 hours. This long exposure to air can cause problems with degradation and stabilizer depletion. This can be avoided with an inert atmosphere. In addition monofilament formulations with much higher than normal stabilization (for example 0.3 to 1.5 wt. % antioxidants) may be needed in some instances.

In one embodiment, a method for building a three-dimensional reduced density articles in an extrusion-based digital manufacturing system, the method comprising: providing a consumable filament of the polymeric material such as the a thermoplastic polycarbonate composition of our invention to the extrusion-based digital manufacturing system, the consumable filament having a length, an exterior surface, and a plurality of tracks along at least a portion of the length, wherein the plurality of tracks provide a fractal dimensionality for at least a portion of the exterior surface that is greater than two for a suitable length scale, e.g., a length scale between 0.01 millimeters and 1.0 millimeter; engaging teeth of a rotatable drive mechanism retained by the extrusion-based digital manufacturing system with the plurality of tracks of the consumable filament; feeding successive portions of the consumable filament with the rotatable drive mechanism to a liquefier retained by the extrusion-based digital manufacturing system, wherein successive teeth of the rotatable drive mechanism are continuously engaged with successive tracks of the plurality of tracks while feeding the successive portions of the consumable filament; melting the consumable filament in the liquefier to provide a melted consumable material; extruding the melted consumable material from the liquefier; and depositing the extruded consumable material in a layer-bylayer manner to form at least a portion of the reduced density article, which can generate back pressure in the liquefier. The consumable filament can be made by any suitable geometry. In one embodiment, the consumable filament has a substantially cylindrical geometry with an average diameter ranging from about 1.1 millimeters to about 2.6 millimeters. In another embodiment, the consumable filament has a substantially rectangular cross-sectional profile. The plurality of tracks can be selected from the group consisting of rectangular tracks, parabolic tracks, worm-type tracks, corrugated tracks, textured tracks, impressed file-type tracks, herringbone-type tracks, sprocket tracks, edge-facing tracks, staggered tracks, and combinations thereof.

As such, one embodiment in which the article having improved resistance to dripping is made in an extrusion-based digital manufacturing system, the method comprising: providing a consumable filament of a thermoplastic polymeric material, (e.g., a thermoplastic polycarbonate composition), to the extrusion-based digital manufacturing system, the consumable filament having a length, an exterior surface, and a plurality of tracks along at least a portion of the length, wherein the plurality of tracks provide a fractal dimensionality for at least a portion of the exterior surface that is greater than two for a length scale between 0.01 millimeters and 1.0 millimeter; engaging teeth of a rotatable drive mechanism retained by the extrusion-based digital manufacturing system with the plurality of tracks of the consumable filament; feeding successive portions of the consumable filament with the rotatable drive mechanism to a liquefier retained by the extrusion-based digital manufacturing system, wherein successive teeth of the rotatable drive mechanism are continuously engaged with successive tracks of the plurality of tracks while feeding the successive portions of the consumable filament; melting the consumable filament in the liquefier to provide a melted consumable material; extruding the melted consumable material from the liquefier; and depositing the extruded consumable material in a layer-by-layer manner to form at least a portion of the reduced density article. A suitable apparatus for carrying out this method is disclosed in U.S. Pat. No. 8,236,227, the entire disclosure of which is herein incorporated by reference.

In another embodiment, the invention relates to a method for producing a three-dimensional object such as the AM article of this invention in direct construction sequence by additive construction from a solidifiable material, such as flame retardant compositions disclosed herein, which is either present in the starting state in a fluid phase or can be liquefied. The direct construction sequence multiple material components are discharged alternately in a programmable manner by means of multiple discharge units and, already joined to one another as a result of the discharge, configure different parts of the object, such that the geometric proportions obtained during discharge already correspond to the object, and where the material components between each other form either edge regions merging into one another without boundaries or boundary regions of the different material components abutting one another without joining. In such a method, the additive construction can occur from layer to layer. The solidifiable material can be discharged in the form of drops as the smallest discharge quantity. The drops can be joined together in a positive-locking manner in one embodiment. In another embodiment, a different material component is placed next to one another drop by drop. The drops can be joined together in a positive-locking manner. In an embodiment, there is discharged in the edge region or boundary region a material component forming an intermediate layer and configured as a separable connection between the materials adjoining the intermediate layer. A predetermined spacing or a clearance between the parts of the object adjoining the intermediate layer can be set by means of the intermediate layer. Such methods for making reduced density articles can be modified variants of the method disclosed in US20130071599, incorporated herein by reference in its entirety. A suitable device for carrying out such methods for making reduced density articles can be found in U.S. Pat. No. 8,292,610, which is incorporated herein by reference in its entirety.

Besides the above-noted orientation characteristics, the present AM articles having improved resistance to dripping when burned have certain void characteristics in that they have a micro structure as measured by optical microscopy containing from 1% to 20% by volume of voids wherein at least 80% of the voids are high aspect voids and less than 20% of the voids are spherical voids with a diameter of 10 to 100 microns. In one embodiment, at least 90% of the voids are high aspect voids and less than 10% of the voids are spherical voids with a diameter of 10 to 100 microns. In other embodiment, least 20% of the voids are angular voids having a cusp angle that is an acute angle of 60 degrees or less. Specific gravity can be measured by ASTM method D792. Voids can be examined by optical microscopy.

In some embodiments, the present AM articles also have a tensile strength at yield of greater than 5,000 psi, and a flex modulus at 100° C. greater than 1,000 psi. Tensile strength can be measured on 3.2 mm thick AM bars as per ASTM method D638. Flexural strength can likewise be measured by ASTM method D790 or by Dynamic Mechanical Analysis (DMA) as per ASTM D4065-01.

As mentioned above, the present AM articles having improved resistance to dripping when burned, besides having the above-noted orientation and voids characteristics, are made from selected thermoplastic polymer compositions. These thermoplastic polymers can comprise either the combination of a thermoplastic polymer with a flame retardant compound, a thermoplastic polymer having flame resistant properties, or a combination thermoplastic polymer having flame resistant properties with a flame retardant compound.

The thermoplastic polymers useful in these AM articles can be amorphous thermoplastic polycarbonate, acrylonitrile butadiene styrene (ABS), polyetherimide (PEI), polyethersulfone (PES), polysulfone (PSu), polyphenylene oxide (PPO), polyphenylene ether (PPE), polyphenylene ether sulfone (PPSU), styrene-acrylonitrile (SAN), or silicone polycarbonate copolymers, or any combination thereof. In one embodiment, the thermoplastic polymer is polycarbonate as defined above.

In one instance, the thermoplastic polymer composition may comprise a polycarbonate blended with either acrylonitrile butadiene styrene (ABS), polyetherimide (PEI), styrene-acrylonitrile (SAN), polytetrafluoroethylene (PTFE) polybutylene terephthalate (PBT), polyethylene terephthalate (PET), or phenyl cyclohexyl dimethanol terephthalate (PCT), or combinations thereof.

In some embodiments, the thermoplastic polymer composition has a bromine and/or chlorine content of less than or equal to 100 parts per million by weight (ppm), based on the total parts by weight of the composition, excluding any filler.

In some embodiments that comprise a flame retardant, the flame retardant can be chosen from a brominated thermoplastic resin, a non-brominated phosphate compound, a phosphinate salt, $C_{1-16}$ sulfonate salt, or a combination thereof.

The amount of flame retardant should be present in an amount at least sufficient to reduce the flammability of the thermoplastic polymer composition, preferably to a UL94 V-0 rating. The amount will vary with the nature of the thermoplastic polymer and with the efficiency of that particular flame retardant. In general, however, the amount of flame retardant, for example a brominated or phosphorous containing FR, will be from 2 to 20 percent by weight based on the weight of thermoplastic polymer. In other embodiments, the range will be from about 5 to 15 percent.

The types of brominated thermoplastic resin flame retardants may vary greatly. They include chosen from brominated polycarbonates, brominated epoxies, brominated phenoxy resins, brominated phthalimides, brominated polystyrenes, brominated acrylates or mixtures thereof. In some embodiments, the brominated thermoplastic resin has an average molecular weight of at least 1000 Mw. And, in other embodiments, the brominated thermoplastic compound contains less than 100 ppm of any brominated diphenyl ether, for example decabromo diphenyl ether, octabromo diphenyl ether or mixtures thereof.

Typically brominated aromatic flame retardants include tetrabromobisphenol A polycarbonate oligomer, polybromophenyl ether, brominated polystyrene, brominated BPA polyepoxide, brominated imides, brominated polycarbonate, poly (haloaryl acrylate), poly (haloaryl methacrylate), or mixtures thereof. Examples of poly (haloaryl acrylates) are poly (bromoaryl acrylate) and poly (pentabromobenzyl acrylate). The brominated flame retardant polymeric flame-retardant material is incorporated into the thermoplastic polymer composition during processing to impart flame retardant characteristics. Exemplary brominated flame retardants are described in U.S. Pat. No. 5,863,974, which is incorporated herein by reference in its entirety.

Examples of other suitable flame retardants are brominated polystyrenes such as polydibromostyrene and polytribromostyrene, decabromobiphenyl ethane, tetrabromobiphenyl, brominated alpha, omega-alkylene-bis-phthalimides, e.g. N,N'-ethylene-bis-tetrabromophthalimide, oligomeric brominated carbonates, especially carbonates derived from tetrabromobisphenol A, which, if desired, are end-capped with phenoxy radicals, or with brominated phenoxy radicals, or brominated epoxy resins. Other aromatic carbonate flame retardants are set forth in U.S. Pat. No. 4,636,544 to Hepp, which is incorporated herein by reference in its entirety.

The types of non-brominated phosphate compounds useful as flame retardants may vary greatly. In some embodiments, the non-brominated phosphate compound is chosen from an organic phosphate compound, an organic compound containing phosphorus-nitrogen bond and mixtures thereof. The organic phosphate compound is an aromatic phosphate of the formula $(GO)_3P=O$, wherein each G is independently an alkyl, cycloalkyl, aryl, alkylaryl, or aralkyl group, provided that at least one G is an aromatic group. In particular, the organic phosphate compound can be triphenyl phosphate, tricresyl phosphate, isopropylated triphenyl phosphate, resorcinol tetraphenyl diphosphate (RDP), the bis (diphenyl) phosphate of hydroquinone and the bis(diphenyl) phosphate of bisphenol A, or their oligomeric and polymeric counterparts, and mixtures thereof. In particular, the non-brominated phosphate compound is an organic compound containing phosphorus-nitrogen bond. Exemplary flame retardant additives are described in U.S. Pat. No. 6,605,659, which is incorporated herein by reference in its entirety.

Additionally, organophosphorus compounds may be suitable as an added flame retardant for the compositions of the present invention. Known compounds including monophosphate esters such as, for example, triphenyl phosphate, tricresyl phosphate, tritolyl phosphate, diphenyl tricresylphosphate, phenyl bisdodecyl phosphate, ethyl diphenyl phosphate, as well as diphosphate esters and oligomeric phosphates such as, for example, resorcinol diphosphate, diphenyl hydrogen phosphate, 2-ethylhexyl hydrogen phosphate have been found to be useful. Suitable oligomeric phosphate compounds are set forth in co-assigned U.S. Pat. No. 5,672,645 the disclosure of which is hereby incorporated herein by reference. In addition, melamine polyphosphate, melamine cyanurate, melamine pyrophosphate, or melamine phosphate can be useful as flame retardants.

In some embodiments, a phosphinate salt can be used as a flame retardant. Phosphinates and diphosphinates include those set forth in U.S. Pat. No. 6,255,371 to Schosser et al., which is incorporated herein by reference in its entirety. Specific phosphinates mentioned include aluminum diethylphosphinate (DEPAL), and zinc diethylphosphinate (DEPZN). Exemplary flame retardant additives are described in U.S. Pat. No. 6,605,659, which is incorporated herein by reference in its entirety.

In some instances, a flame retarding amount of a $C_{1-16}$ salt of a substituted sulfonic acid can be used as the flame retardant. Preferred salt forming metals are selected from the group consisting of periodic table Group IA (alkaline) and Group IIA (alkaline earth) metals, more preferred metals are selected from the group consisting of Group IA (alkaline) metals. One suitable $C_{1-16}$ sulfonate salts are alkali metal C1 to C4 perfluoro sulfonates.

In some embodiments, it can be useful to add a nitrogen adjuvant to the thermoplastic polymer composition. These include a flame retarding quantity of one or a mixture of nitrogen-containing flame retardants such as triazines, guanidines, cyanurates, and isocyanurates. Preferred triazines include 2,4,6-triamine-1,3,5-triazine (melamine, CAS Reg. No. 108-78-1), melamine derivatives (CAS Reg. No. 645-92-1), ammelide (CAS Reg. No. 645-93-2), 2-ureidomelamine, acetoguanamine (CAS Reg. No. 542-02-9), benzoguanamine (CAS Reg. No. 91-76-9), and the like. Salts/adducts of these compounds with boric acid or phosphoric acid may be used in the composition. Examples include melamine pyrophosphate and melamine polyphosphate. Preferred cyanurate/isocyanurate compounds include salts/adducts of the triazine compounds with cyanuric acid, such as melamine cyanurate and any mixtures of melamine salts. Preferred guanidine compounds include guanidine; aminoguanidine; and the like; and their salts and adducts with boric acid, carbonic acid, phosphoric acid, nitric acid, sulfuric acid, and the like; and mixtures comprising at least one of the foregoing guanidine compounds. These nitrogen-containing flame retardant can be present in the thermoplastic polymer composition at 1 to 25 weight percent, based on the total weight of the composition.

Some flame retardants, for example, brominated and chlorinated flame retardants, are typically used with a synergist, particularly inorganic antimony compounds. Such compounds are widely available or can be made in known ways. Typical, inorganic synergist compounds include $Sb_2O_5$; $SbS_3$; and the like. Especially preferred is antimony trioxide ($Sb_2O_3$). Synergists such as antimony oxides are typically used at about 0.5 to 15, and more preferably from 1 to 6 percent by weight based on the weight percent of resin in the final composition. These nitrogen-containing flame retardant can be present in the thermoplastic polymer composition at 1 to 25 weight percent, based on the total weight of the composition.

Also, the composition may contain polytetrafluoroethylene (PTFE) type resins or copolymers used to reduce dripping in flame retardant thermoplastics. The fluoropolymers are capable of being fibrillated ("fibrillatable") during mixing, individually or collectively, with the polyester. "Fibrillation" is a term of art that refers to the treatment of fluoropolymers to produce, for example, a "node and fibril," network, or cage-like structure. Suitable fluoropolymers include but are not limited to homopolymers and copolymers that comprise structural units derived from one or more fluorinated alpha-olefin monomers, that is, an alpha-olefin monomer that includes at least one fluorine atom in place of a hydrogen atom. In one embodiment, the fluoropolymer comprises structural units derived from two or more fluorinated alpha-olefin, for example tetrafluoroethylene, hexafluoroethylene, and the like. In another embodiment, the fluoropolymer comprises structural units derived from one or more fluorinated alpha-olefin monomers and one or more non-fluorinated monoethylenically unsaturated monomers that are copolymerizable with the fluorinated monomers. Examples of suitable fluorinated monomers include and are not limited to alpha-monoethylenically unsaturated copolymerizable monomers such as ethylene, propylene, butene, acrylate monomers (e.g., methyl methacrylate and butyl acrylate), vinyl ethers, (e.g., cyclohexyl vinyl ether, ethyl vinyl ether, n-butyl vinyl ether, vinyl esters) and the like. Specific examples of fluoropolymers include polytetrafluoroethylene, polyhexafluoropropylene, polyvinylidene fluoride, polychlorotrifluoroethylene, ethylene tetrafluoroethylene, fluorinated ethylene-propylene, polyvinyl fluoride, and ethylene chlorotrifluoroethylene. Combinations of the foregoing fluoropolymers can also be used. Fluoropolymers are available in a variety of forms, including powders, emulsions, dispersions, agglomerations, and the like. "dispersion" (also called "emulsion") fluoropolymers are generally manufactured by dispersion or emulsion, and generally comprise about 25 to 60 weight % fluoropolymer in water, stabilized with a surfactant, wherein the fluoropolymer particles are approximately 0.1 to 0.3 micrometers in diameter. "fine powder" (or "coagulated dispersion") fluoropolymers can be made by coagulation and drying of dispersion-manufactured fluoropolymers. Fine powder fluoropolymers are generally manufactured to have a particle size of approximately 400 to 500 micrometers. "Granular" fluoropolymers can be made by a suspension method, and are generally manufactured in two different particle size ranges, including a median particle size of approximately 30 to 40 micrometers, and a high bulk density product exhibiting a median particle size of about 400 to 500 micrometers. Pellets of fluoropolymer may also be obtained and cryogenically ground to exhibit the desired particle size.

In one embodiment, the fluoropolymer is encapsulated by a rigid copolymer, e.g., a copolymer having a Tg of greater than 10C and comprising units derived from a monovinyl aromatic monomer and units derived from a $C_{3-6}$ monovinylic monomer. In a specific embodiment, the monovinylic aromatic monomer is styrene, alpha-methyl styrene, dibromostyrene, vinyltoluene, vinylxylene, butylstyrene, or methoxystyrene, specifically styrene and the monovinylic monomer is acrylonitrile, methacrylonitrile, methyl(meth) acrylate, ethyl(meth)acrylate, n-propyl(meth)acrylate, or isopropyl(meth)acrylate, specifically acrylonitrile. A useful encapsulated fluoropolymer is PTFE encapsulated in styrene-acrylonitrile (SAN), also known as TSAN. Exemplary encapsulated fluoropolymers are described in U.S. Pat. No. 5,521,230. In some instances, especially in polycarbonate, polyester carbonate, polyetherimide and mixtures thereof, formulations comprising alkali and alkaline earth metal sulfonate salts are effective flame retardant additives. In some particular embodiments suitable sulfonate salts comprise perfluoroalkyl(alkali metal/alkaline earth metal) sulfonate salts, e.g., potassium perfluorobutyl sulfonate salt (KPFBS). Possible sulfonate salts include potassium sulfone sulfonate (KSS), sodium benzene sulfonate, and sodium dodecylbenzene sulfonate (NaDBS), potassium trifluoromethyl sulfonate and the like. Desirably, the perfluoroalkyl alkaline metal/alkaline earth metal sulfonate salts have less than or equal to eight carbon atoms. Mixtures comprising at least one of any of the above mentioned sulfonate salts may also be employed. Generally, the sulfonate salt(s) are present in the composition in an amount of less than or equal to about 5.0 weight percent (wt %), e.g., about 0.001 wt % to about 5.0 wt %, based upon the total weight of the composition, specifically, about 0.005 wt % to about 3.0 wt %, more specifically about 0.01 wt % to about 2.0 wt %, even more specifically about 0.01 wt % to about 1.0 wt %, yet more specifically about 0.025 wt % to about 0.5 wt %, and even more specifically about 0.025 wt % to about 0.08 wt %. All weight percent discussed herein are based upon the total weight of the composition unless otherwise specified.

In some embodiments, a thermoplastic resin having flame resistant properties can be used instead of or with the combination of a thermoplastic polymer with a flame retardant. The thermoplastic resin having flame resistant properties may comprise a polyetherimide, a silicone polyetherimide copolymer, a resorcinol polyester carbonate, a silicone resorcinol polyester carbonate copolymer, a polysulfone, a polyethersulfone, a polyphenylene ether sulfone or any mixture thereof. Examples of such flame resistant resin combinations, which are largely independent of additive technology for their flame resistance, are described in U.S. Pat. No. 5,387,639; 7,652,107; 7,790,292; 7,932,310; 8,017,699; 8,309,637 and 8,349,933 which are incorporated herein by reference in their entirety. Resorcinol based polyester carbonates are further described in U.S. Pat. Nos. 7,452,944 and 7,652,107 which are also incorporated herein by reference in their entirety.

Blends of polyetherimides, polysulfones and resorcinol based polyester carbonate with a low level, 0.1 to 5.0 wt. %, of a silicone copolymer are not only effective in meeting UL flammability tests but are especially effective in meeting flame retardant requirement for aircraft application s with low heat release. Heat release testing can be done using the Ohio State University (OSU) rate-of-heat release apparatus, as measured by the method listed in FAR 25.853. The heat release test methods are also described in the "Aircraft Materials Fire Test Handbook" DOT/FAA/AR-00/12, Chapter 5 "Heat Release Test for Cabin Materials".

Flammability tests described in the Examples below were performed with the procedure of Underwriter's Laboratory Bulletin 94 entitled "Combustion Tests for Classification of Materials, UL-94." According to this procedure, the materials were classified as either UL-94 V-0, UL-94 V-1 or UL-94 V-2 on the basis of the tests results obtained for ten samples. The criteria for each of these flammability classifications according to UL-94, are, briefly, as follows: V-0: the average period of flaming and/or smoldering after removing the igniting flame should not exceed five seconds and none of the samples should produce drips of particles which ignite absorbent cotton. V-1: the average period of flaming and/or smoldering after removing the igniting flame should not exceed twenty-five seconds and none of the samples should produce drips of particles which ignite absorbent cotton. V-2: the average period of flaming and/or smoldering after removing the igniting flame should not exceed twenty-five seconds and the samples may produce drips of burning particles which ignite absorbent cotton. In some instances the drip resistant AM parts further be able to pass the UL94 5-VA or 5VB test, or both UL-94 5VA and 5VB criteria or V-0, 5V-A and 5V-B criteria.

In yet other instances the drip resistant AM parts further be able to pass the Federal Aviation Regulation (FAR) 25.853 requirements. In this test, sometimes referred to as the Ohio State University (OSU) rating, the amount of energy released after 2 minutes and the peak heat release energy are measured. Lower heat release values are desirable. For many aerospace and transportation applications, materials are required to have a rating of 65/65 (2 minute heat release/peak heat release) or less. In other instances the antidrip AM part will have a rating of 55/55 or less. In general, it is desirable to have a material demonstrate a resistance to burn and achieve low OSU ratings. In addition, the time it takes to obtain peak heat release is another material characteristic that has significance since it correlates to the time people, such as passengers, crew, and others, have to flee the hazardous conditions. A time to peak heat release of more than 150 seconds, as measured by FAR 25.853 (OSU test) is desirable, In other instances the AM antidrip part will have an NBS (National Bureau of Standards) optical smoke density with flame of less than 5 when measured at four minutes, based on ASTM E-662 (FAR/JAR 25.853).

In addition, the antidrip AM part may be made of thermoplastic polymer compositions that can contain one or more colorants. For example: Solvent Green 3, Solvent Green 28, Solvent Green 38, Pigment Green 50, Pigment Green 36, Solvent Red 52, Solvent Red 101, Solvent Red 111, Solvent Red 135, Solvent Red 169, Solvent Red 179, Solvent Red 207, Pigment Red 101, Disperse Red 22, Vat Red 41, Solvent Orange 60, Solvent Orange 63, Disperse Orange 47, Solvent Violet 13, Solvent Violet 14, Solvent Violet 36, Solvent Violet 50, Disperse violet 26/31, Pigment Blue 29, Pigment Blue 60, Copper Phthalocyanine Pigment Blue 15.4, Disperse Blue 73, Solvent Blue 97, Solvent Blue 101, Solvent Blue 104, Solvent Blue 122, Solvent Blue 138, Pigment Yellow 53, Pigment Yellow 138, Pigment Yellow 139, Disperse Yellow 201, Solvent Yellow 33, Solvent Yellow 114, Solvent Yellow 93, Solvent Yellow 98, Solvent Yellow 163, Solvent Yellow 160:1, Solvent Yellow 188, Pigment Brown 24, Amino Ketone Black, chrome oxides, carbon black, channel black, Pigment Black 6, zinc sulfide, zinc oxide, titanium dioxide ($TiO_2$), and mixtures thereof. Colorants of particular note are: Solvent Violet 36, Pigment Blue 60, Pigment Blue 15:1, Pigment Blue 15.4, carbon black, titanium dioxide or any combination.

The composition of the AM antidrip article may also comprise a stabilizer. The stabilizer can be present in an amount of from 0.05 to 1.0 percent by weight. Stabilizers include, antioxidants such as phosphites, phosphonites, thioesters and hindered phenols, which can be used alone, or more effectively, in combination with each other. Phosphorus containing stabilizers including triaryl phosphite and aryl phosphonates are of note as useful additives. Difunctional phosphorus containing compounds can also be employed. Stabilizers with a molecular weight of greater than or equal to about 300 are preferred for lower volatility. In other instances phosphorus containing stabilizers with a molecular weight of greater than or equal to 500 are useful. Stabilizers with low volatility are needed so that they are retained in the polymer during part forming. The stabilizer can be a tri-aryl phosphite.

The composition may also comprise ingredients ordinarily incorporated into polymer compositions can be used, with the proviso that the additives are selected so as to not significantly adversely affect the desired antidrip and flame retardant properties of the article. Such additives can be mixed at a suitable time during the mixing of the components for forming the composition. Possible additives include impact modifiers, fillers, reinforcing agents, antioxidants, heat stabilizers, light stabilizers, ultraviolet light (UV) absorbers (such as benzotriazoles), plasticizers, lubricants, mold release agents, antistatic agents, colorants, blowing agents, and radiation stabilizers. Combinations of additives can be used, for example an antioxidant, a UV absorber, and a mold release agent. The total amount of additives (other than any impact modifier, filler, or reinforcing agents) is generally 0.1 to 5.0 wt. %, based on the total weight of the composition.

The following examples are included to provide additional guidance to those skilled in the art. The examples provided are merely representative are not intended to limit the invention, as defined in the appended claims, in any manner. Letters designate comparative examples, numbers designate examples of the invention.

PEI Blend Examples

A series of 127×3.2 mm flame bars were prepared by a monofilament manufacturing (MM) technique. The bars were made from a 1.8 mm monofilament comprising a blend of: 49.9 wt. % polyetherimide (ULTEM 1000), 39.0 wt. % of a 90/10 mole ratio resorcinol:bisphenol-A 1:1 iso:tere phthalate polyestercarbonate (LEXAN SLX9010), 8.0 wt. % of a BPA silicone polycarbonate copolymer with 20% of a D35 dimethylsiloxane), 3.0 wt. % of silicone polyetherimde copolymer with 43% of D10 dimethylsiloxane) and 0.1 wt. % of a tris di-tertbutyl phenyl phosphite stabilizer. In its solid void free injection molded version this composition is a known flame retardant material. However we discovered that articles made from the resin blend via monofilament additive manufacturing had a tendency to drip when flame was applied. This dripping caused a reduction in performance in flame resistance tests.

Dripping is a critical failure mode in FR tests since dripping removes material from the flame area providing a thinner barrier of char protection, additionally any flaming drips can spread a small fire increasing the danger and damage. A longer time to the onset of dripping is desirable. The monofilament manufactured (MM) parts showed a greater tendency to drip than injection molded parts. We investigated the details of the construction of the MM parts and discovered that the orientation of the monofilament strands in different construction had a surprising effect on dripping.

A series of parts were constructed in a Stratasys Fortus 400MC additive manufacturing machine using the same PEI blend as described above starting with a ~1.75 mm diameter monofilament. Between ten and fourteen layers were used to make flame bars. Due to attenuation of the monofilament during part build at the final layers were ~0.28 mm. The bars were fabricated with a nozzle monofilament extrusion temperature of ~380 to 400 C with an oven consolidation temperature of ~180 to 190 C. The monofilament additive manufactured parts were characterized by optical microscopy and found to have more than 1 volume % voids and that more than 80 vol. % of the voids were high aspect voids with a length to diameter ratio of greater than 1. At least 20 vol. % of the voids had an acute cusp angle of 60 degrees or less.

The experiment involved changing the direction of alternate layers.

The orientations are as follows (see Table 1 below and FIGS. 1 to 4):

90×90 (degrees) has layers in the same direction all deposited across the short axis of the bar no change as the layers were deposited on top of each other.

0×0 (degrees) has the monofilament running the length (long axis) of the bars with no change as the layers were deposited on top of each other.

0×90 (degrees) has the first layer following the long axis of the bar and the next layer deposited at a 90 degree angle to the first layer across the short axis of the bar. The bar was built in alternating layers long axis over short axis. This made a square checked pattern when looking down on the layers under magnification.

45×135 (degrees) has the first layer deposited at a 45 degree angle to the long axis of the bar. The next layer is deposited at a 135 degree angle to the long axis making an X type crossing pattern with alternating layers orthogonal to each other. From above they gave a diamond pattern under magnification.

Samples (4 bars of each construction) were conditioned for >48 hrs. at 50% relative humidity at ~23° C. and then burned under the UL-94 5VB flame test. This test used a large flame applied for 5 seconds, removed for 5 seconds and reapplied until the samples dripped. During a flame test, where temperatures are above 400° C., where the strands comprising the bar melt, ignite, burn and char one might expect similar performance independent of construction orientation.

While the samples all had good char formation and short flame out times, as expected from this formulation, they had variation in the time to drip.

Based on type of construction we found (Table 1) that the 0×0 orientation (Example 1) had the most resistance to dripping (94.8 sec.). Surprisingly the 90×90 orientation (Comparative Example A) that exposed the side of piled/stacked monofilaments was the worst with a time to drip of 81.2 sec.

The alternating angled orientations (0×90 and 45×135, Examples 2 and 3) that exposed less of the side of the monofilament to the flame had intermediate times to drip of 85.8 and 84.8 seconds. The 0×0 orientation that had the least monofilament side exposed had the most resistance to dripping. It seems the less exposure of the side of the monofilament to the flame the lower the tendency to drip. Construction of the part as well as the material of construction are both important to flame retardant performance.

TABLE 1

PEI Blend UL94 5VB FR Testing

| Examples | Example A | Example 1 | Example 2 | Example 3 |
|---|---|---|---|---|
| alternate layer orientation | 90 × 90 | 0 × 0 | 0 × 90 | 45 × 135 |
| Avg. time to drip (sec.) | 81.2 | 93.8 | 85.8 | 84.8 |

Polycarbonate Examples

A series of 127×3.2 mm flame bars were prepared by a monofilament manufacturing (MM) technique. The bars were made from a 1.8 mm monofilament comprising a blend of: bisphenol A polycarbonate (PC) with 0.03 wt. % tris di-tert butyl phenyl phosphite, 0.15 wt. % pentaerythritol tetrastearate (PETS) processing aid, 2 ppm of solvent violet 36 and 1 ppm of pigment blue 60 colorants. The PC had a weight average molecular weight (Mw) of 22,000. In its solid void free injection molded version this composition is a known to have some flame retardant capability at this thickness. However we discovered that articles made from the resin blend via monofilament additive manufacturing had a tendency to drip when flame was applied. This dripping may cause a reduction in performance in flame resistance tests in this and other polycarbonate formulations.

A series of parts were constructed in a Stratasys Fortus 400MC additive manufacturing machine using a ~1.9 mm diameter polycarbonate monofilament. Between ten and fourteen layers were used to make flame bars. Due to attenuation of the monofilament during part build the final layers were ~0.28 mm. The bars were fabricated with a nozzle monofilament extrusion temperature of ~345 to 365 C with an oven consolidation temperature of ~135 to 145 C. The monofilament additive manufactured parts were characterized by optical microscopy and found to have more than 1 volume % voids and that more than 80 vol. % of the voids were high aspect voids with a length to diameter ratio of greater than 1. At least 20 vol. % of the voids had an acute cusp angle of 60 degrees or less.

As described above the experiment involved changing the direction of alternate layers. The orientations are as follows (see Table 2 below):

90×90 (degrees) has layers in the same direction all deposited across the short axis of the bar no change as the layers were deposited on top of each other.

0×0 (degrees) has the monofilament running the length (long axis) of the bars with no change as the layers were deposited on top of each other.

0×90 (degrees) has the first layer following the long axis of the bar and the next layer deposited at a 90 degree angle to the first layer across the short axis of the bar. The bar was built in alternating layers long axis over short axis. This made a square checked pattern when looking down on the layers under magnification.

45×135 (degrees) has the first layer deposited at a 45 degree angle to the long axis of the bar. The next layer is deposited at a 135 degree angle to the long axis making an X type crossing pattern with alternating layers orthogonal to each other. From above they gave a diamond pattern under magnification.

Samples (3 bars of each construction) were conditioned for >48 hrs. at 50% relative humidity at ~23° C. and then burned under the UL-94 VX flame test. This test used a small flame applied for 5 seconds, removed until the flame went out and then reapplied for 5 seconds. A longer time to the onset of dripping is desirable. During a flame test, with temperatures above 400° C., where the strands comprising the bar melt, ignite, burn and char one might expect similar performance independent of construction orientation.

Surprisingly the samples showed a significant variation the time to drip based on type of construction. We found (Table 2) that the 45×135 orientation (Example 6) had the most resistance to dripping (9.4 sec.). The 90×90 (Comparative Example B) orientation that exposed the side of piled/stacked monofilaments was the worst rapidly dripping with a time to drip of only 3.4 sec.

TABLE 2

| PC UL94 VX FR Testing | | | | |
| --- | --- | --- | --- | --- |
| Examples | Example B | Example 4 | Example 5 | Example 6 |
| alternate layer orientation | 90 × 90 | 0 × 0 | 0 × 90 | 45 × 135 |
| Avg. time to drip (sec.) | 3.4 | 8.8 | 6.8 | 9.4 |

The alternating angled orientations (0×90 and 0×0, Examples 5 and 4) that exposed less of the side of the monofilament to the flame had intermediate times to drip of 6.8 and 8.8 seconds. The 45×135 orientation had the most resistance to dripping.

Even this non-flame retardant polycarbonate formulation (no halogen or sulfonate salt added) the orientation of the mono filament layers had a large effect on dripping; with the 45×135, 0×90 and 0×0 orientations having at least 2× or more resistance (longer time) to dripping than the 90×90 orientation.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The present invention is further illustrated by the following Embodiments.

Embodiment 1

A process for making an article by additive manufacturing having a resistance to dripping when burned comprising (1) depositing a multitude of thermoplastic monofilament strands each having a diameter from 0.1 to 20.0 mm using a fused deposition modeling apparatus in a pattern and (2) fusing the multitude of strands together to make an article of manufacture having voids therein; wherein the article of additive manufacture comprises a thermoplastic polymer composition, the article of manufacture having (a) at least 50% of the monofilament strands oriented within 45 degrees of the long part of the axis; (b) the multitude of strands is greater than 10; (c) a micro structure as measured by optical microscopy containing from 1% to 20% by volume of voids wherein at least 80% of the voids are high aspect voids and less than 20% of the voids are spherical voids with a diameter of 10 to 100 microns; and (d) wherein the thermoplastic polymer composition comprises either the combination of a thermoplastic polymer with a flame retardant compound, a thermoplastic resin having flame resistant properties, or a combination of a thermoplastic resin having flame resistant properties with a flame retardant compound.

Embodiment 2

The process of claim 1 wherein the depositing of monofilaments occurs in a pattern of alternating layers crossing each other at an angle of from 60 to 120 degrees.

Embodiment 3

The process of claim 1 wherein the depositing of monofilaments occurs in a pattern of alternating layers crossing each other at an angle of from 85 to 95 degrees.

Embodiment 4

The process of claim 1 wherein the depositing of monofilaments occurs in a pattern of alternating layers crossing each other at an angle of from 60 to 120 degrees and at least half of said monofilaments are oriented from 1.0 to 45 degrees of the longest axis of the part.

Embodiment 5

The process of claim 1 wherein the depositing of monofilaments occurs in a pattern of alternating layers crossing each other at an angle of from 60 to 120 degrees and at least half of said monofilaments are oriented to be parallel to the longest axis of the part.

Embodiment 6

The process of any of claims 1-5 wherein at least 90% of the voids are high aspect voids and less than 10% of the voids are spherical voids with a diameter of 10 to 100 microns.

Embodiment 7

The process of any of claims 1-6 wherein least 20% of the voids are angular voids having an cusp angle that is an acute angle of 60 degrees or less.

Embodiment 8

The process of any of claims 1-7 wherein the article has a tensile strength at yield of greater than 5,000 psi, and a flex modulus at 100° C. greater than 1,000 psi.

Embodiment 9

The process of any of claims 1-8 wherein the thermoplastic polymer is a combination of a thermoplastic polymer with a flame retardant compound.

Embodiment 10

The process of claim 9 wherein the flame retardant compound is chosen from a brominated thermoplastic resin, a non-brominated phosphate compound, a phosphinate salt, C1-16 sulfonate salt, or a combination thereof.

Embodiment 11

The process of claim 9 wherein the flame retardant compound is a brominated thermoplastic resin.

Embodiment 12

The process of claim 11 wherein the brominated thermoplastic resin is chosen from brominated polycarbonates, brominated epoxies, brominated phenoxy resins, brominated phthalimides, brominated polystyrenes, brominated acrylates or mixtures thereof.

Embodiment 13

The process of either claim 11 or 12 wherein the brominated thermoplastic resin has an average molecular weight of at least 1000 Mw.

Embodiment 14

The process of any of claims 11-13 wherein the brominated thermoplastic resin contains less than 100 ppm of any brominated diphenyl ether.

Embodiment 15

The process of claim 9 wherein the flame retardant compound is a non-brominated phosphate compound.

Embodiment 16

The process of claim 15 wherein the non-brominated phosphate compound is chosen from an organic phosphate compound, an organic compound containing phosphorus-nitrogen bond and mixtures thereof.

Embodiment 17

The process of claim 16 wherein the organic phosphate compound is an aromatic phosphate of the formula $(GO)_3P=O$, wherein each G is independently an alkyl, cycloalkyl, aryl, alkylaryl, or aralkyl group, provided that at least one G is an aromatic group.

Embodiment 18

The process of claim 17 wherein the organic phosphate compound triphenyl phosphate, tricresyl phosphate, isopropylated triphenyl phosphate, resorcinol tetraphenyl diphosphate (RDP), the bis(diphenyl) phosphate of hydroquinone, the bis(diphenyl) phosphate of bisphenol A, and mixtures thereof.

Embodiment 19

The process of claim 17 wherein the non-brominated phosphate compound is an organic compound containing phosphorus-nitrogen bond.

Embodiment 20

The process of claim 9 wherein the flame retardant compound is a phosphinate salt.

Embodiment 21

The process of claim 9 wherein the flame retardant compound is a C1-16 sulfonate salt.

Embodiment 22

The process of claim 21 wherein the C1-16 sulfonate salt is an alkali metal C1 to C4 perfluoro sulfonate.

Embodiment 23

The process of any of the claims 1 to 22 wherein the thermoplastic polymer is an amorphous thermoplastic polycarbonate, acrylonitrile butadiene styrene (ABS), polyetherimide (PEI), polyethersulfone (PES), polysulfone (PSu), polyphenylene oxide (PPO), polyphenylene ether (PPE), polyphenylene ether sulfone (PPSU), styrene-acrylonitrile (SAN), or silicone polycarbonate copolymers, or any combination thereof.

Embodiment 24

The process of any of the claims 1-23 wherein the thermoplastic polymer is a thermoplastic polycarbonate.

Embodiment 25

The process of any of claims 1-24 wherein the thermoplastic polymer is a polycarbonate blended with acrylonitrile butadiene styrene (ABS), polyetherimide (PEI), styrene-acrylonitrile (SAN), polytetrafluoroethylene (PTFE) polybutylene terephthalate (PBT), polyethylene terephthalate (PET), or phenyl cyclohexyl dimethanol terephthalate (PCT), or combinations thereof.

Embodiment 26

The process of any of the claims 1-25 wherein the thermoplastic polymer has a bromine and/or chlorine content of less than or equal to 1000 parts per million by weight (ppm), based on the total parts by weight of the composition, excluding any filler.

Embodiment 27

The process of any of claims 1-8 wherein the thermoplastic polymer is a thermoplastic resin having flame resistant properties.

Embodiment 28

The process of claim 27 wherein the thermoplastic resin having flame resistant properties comprises a polyetherimide, a silicone polyetherimide copolymer, a resorcinol polyester carbonate, a silicone resorcinol polyester carbonate copolymer, a polysulfone, a polyethersulfone, a polyphenylene ether sulfone or any mixture thereof.

Embodiment 29

The process of any of claims 1-8 wherein the thermoplastic polymer is a combination of a thermoplastic resin having flame resistant properties with a flame retardant compound.

Embodiment 30

The process of any of the claims 1-29 wherein the thermoplastic polymer composition further comprises a metal synergist.

Embodiment 31

The process of claim 30 wherein the metal synergist is an antimony compound.

Embodiment 32

The process of claim 31 wherein the antimony compound is antimony oxide.

Embodiment 33

The process of claim 31 wherein the antimony compound is chosen from antimony trioxide, antimony pentoxide and sodium antimonate.

Embodiment 34

The process of any of the claims 31-33 wherein the metal synergist is less than 10 microns in weight average particle size.

Embodiment 35

The process of any of the claims 1-34 wherein the thermoplastic polymer composition further comprises an anti-drip agent.

Embodiment 36

The process of claim 35 wherein the anti-drip agent is chosen from a fibril forming or non-fibril forming fluoropolymer.

Embodiment 37

The process of claim 36 wherein the anti-drip agent is polytetrafluoroethylene (PTFE).

Embodiment 38

The process of claim 37 wherein the polytetrafluoroethylene (PTFE) is encapsulated by a rigid copolymer.

Embodiment 39

The process of claim 38 wherein the rigid copolymer is styrene-acrylonitrile copolymer, polycarbonate, polystyrene, polyphenylene oxide, polymethyl methacrylate or any combination thereof.

Embodiment 40

A reduced density flame resistant article of manufacture made by the process of any of claims 1-39 wherein at least 90% of the voids are high aspect voids and less than 10% of the voids are spherical voids with a diameter of 10 to 100 microns.

Embodiment 41

A reduced density flame resistant article of manufacture made by the process of any of claims 1-39 wherein least 20% of the voids are angular voids having a cusp angle that is an acute angle of 60 degrees or less.

Embodiment 42

A reduced density flame resistant article of manufacture made by the process of any of claims 1-39 wherein the article has a tensile strength at yield of greater than 5,000 psi, and a flex modulus at 100° C. greater than 1,000 psi.

Embodiment 43

A reduced density flame resistant article of manufacture made by the process of any of claims 1-39 further comprising a colorant chosen from solvent violet 36, pigment blue 60, pigment blue 15:1, pigment blue 15.4, carbon black, titanium dioxide or any combination thereof.

Embodiment 44

The reduced density flame resistant article of manufacture of any of claims 40-43 wherein the high aspect voids have an aspect ratio from 2:1 to 100:1 with a major length of less than 5 mm.

Embodiment 45

An article made by additive manufacturing having a resistance to dripping when burned comprising a thermoplastic polymer composition, the article of manufacture having (a) at least 50% of the monofilament strands oriented within 45 degrees of the long part of the axis; (b) the multitude of strands is greater than 10; (c) a micro structure as measured by optical microscopy containing from 1% to 20% by volume of voids wherein at least 80% of the voids are high aspect voids and less than 20% of the voids are spherical voids with a diameter of 10 to 100 microns; and (d) wherein the thermoplastic polymer comprises is either a thermoplastic resin having flame resistant properties, the combination of a thermoplastic polymer with a flame retardant compound, or a combination thermoplastic resin having flame resistant properties with a flame retardant compound.

Embodiment 46

The reduced density flame resistant article of manufacture of claim 45 wherein monofilaments are deposited in a pattern of alternating layers crossing each other at an angle of from 60 to 120 degrees.

Embodiment 47

The reduced density flame resistant article of manufacture of claim 45 wherein the depositing of monofilaments occurs in a pattern of alternating layers crossing each other at an angle of from 85 to 95 degrees.

Embodiment 48

The reduced density flame resistant article of manufacture of claim 45 wherein the monofilaments are deposited in a pattern of alternating layers crossing each other at an angle of from 60 to 120 degrees and at least half of said monofilaments are oriented from 1.0 to 45 degrees of the longest axis of the part.

Embodiment 49

The reduced density a flame resistant article of manufacture of claim 45 wherein monofilaments are deposited in a pattern of alternating layers crossing each other at an angle of from 60 to 120 degrees and at least half of said monofilaments are oriented to be parallel to the longest axis of the part.

Embodiment 50

The reduced density flame resistant article of manufacture of any of claims 45-49 wherein at least 90% of the voids are high aspect voids and less than 10% of the voids are spherical voids with a diameter of 10 to 100 microns.

Embodiment 51

The reduced density flame resistant article of manufacture of any of claims 45-49 wherein least 20% of the voids are angular voids having a cusp angle that is an acute angle of 60 degrees or less.

Embodiment 52

The reduced density flame resistant article of manufacture of any of claims 45-51 wherein the article has a tensile strength at yield of greater than 5,000 psi, and a flex modulus at 100° C. greater than 1,000 psi.

Embodiment 53

The reduced density flame resistant article of manufacture of any of claims 45-52 wherein the thermoplastic polymer is a combination of a thermoplastic resin with a flame retardant compound.

Embodiment 54

The reduced density flame resistant article of manufacture of any of claims 45-52 wherein the thermoplastic polymer is a thermoplastic resin having flame resistant properties.

Embodiment 55

The reduced density flame resistant article of manufacture of claim 54 wherein the thermoplastic resin having flame resistant properties comprises a polyetherimide, a silicone polyetherimide copolymer, a resorcinol polyester carbonate, a silicone resorcinol polyester carbonate copolymer, a polysulfone, a polyethersulfone, a polyphenylene ether sulfone or any mixture thereof.

Embodiment 56

The reduced density flame resistant article of manufacture of any of claims 45-52 wherein the thermoplastic polymer is a combination of a thermoplastic resin having flame resistant properties with a flame retardant compound.

Embodiment 57

The reduced density flame resistant article of manufacture of any of claims 45-52 further comprising a colorant chosen from solvent violet 36, pigment blue 60, pigment blue 15:1, pigment blue 15.4, carbon black, titanium dioxide or any combination thereof.

Embodiment 58

The reduced density flame resistant article of manufacture of any of claims 45-52 wherein the high aspect voids have an aspect ratio from 2:1 to 100:1 with a major length of less than 5 mm.

Embodiment 59

A process for testing the UL-94 flame performance of an article of additive manufacture comprising the steps of: 1) forming a monofilament additive manufactured rectangular part with a width of 0.5 to 2.5 centimeters, a length of at least 10 centimeters, and a thickness of 0.1 to 10 millimeters from a multitude of thermoplastic monofilament strands having a diameter from 0.1 to 20.0 mm using a fused deposition modeling apparatus; the part having (a) at least 50% of the monofilament strands oriented within 45 degrees of the long axis of the part; (b) the multitude of strands is greater than 10; (c) a micro structure as measured by optical microscopy containing from 1% to 20% by volume of voids wherein at least 80% of the voids are high aspect voids and less than 20% of the voids are spherical voids with a diameter of 10 to 100 microns; and (d) wherein the thermoplastic polymer comprises is either a thermoplastic polymer having flame resistant properties, the combination of a thermoplastic polymer with a flame retardant compound, or a combination thermoplastic polymer having flame resistant properties with a flame retardant compound; 2) equilibrating the formed part for at least 24 hours at 50% relative humidity and at 20 to 25 degrees C.;

Embodiment 60

An article made by the process of any of claims 1-39 wherein the article has a resistance to dripping when burned using the method of UL5VB or UL94 at 3.2 mm thickness.

Embodiment 61

An article of any of claims 45-58 wherein the article has a resistance to dripping when burned using the method of UL-5VB or UL-94 at 3.2 mm thickness.

We claim:

1. A process for making an article by additive manufacturing having a resistance to dripping when burned comprising (1) depositing a multitude of thermoplastic monofilament strands each having a diameter from 0.1 to 20.0 mm using a fused deposition modeling apparatus in a pattern and (2) fusing the multitude of thermoplastic monofilament strands together to make an article of manufacture having voids therein; wherein the article of additive manufacture comprises a thermoplastic polymer composition and has a long axis, the article of manufacture having (a) at least 50% of the thermoplastic monofilament strands oriented at an angle of 1.0 to 45 degrees to the long axis of the article; (b) the multitude of thermoplastic monofilament strands is greater than 10 thermoplastic monofilament strands; (c) a micro structure as measured by optical microscopy containing the voids in an amount from 1% to 20% by volume wherein at least 80% of the voids are high aspect voids and less than 20% of the voids are spherical voids with a diameter of 10 to 100 microns; and (d) wherein the thermoplastic polymer composition comprises either the combination of a thermoplastic polymer with a flame retardant compound, a thermoplastic resin having flame resistant properties, or a combination of a thermoplastic resin having flame resistant properties with a flame retardant compound wherein the article is characterized by a resistance to dripping when burned using the method of UL-5VB UL 94 at 3.2 mm thickness.

2. The process of claim 1 wherein the depositing of thermoplastic monofilaments strands occurs in a pattern of alternating layers crossing each other at an angle of from 60 to 120 degrees and at least half of said thermoplastic monofilaments strands are oriented from 1.0 to 45 degrees of the long axis of the article.

3. The process of claim 1 wherein the depositing of thermoplastic monofilaments strands occurs in a pattern of alternating layers crossing each other at an angle of from 60 to 120 degrees and at least half of said thermoplastic monofilaments strands are oriented to be parallel to the long axis of the article.

4. The process of claim 1 wherein at least 90% of the voids are high aspect voids and less than 10% of the voids are spherical voids with a diameter of 10 to 100 microns.

5. The process of claim 1 wherein least 20% of the voids are angular voids having a cusp angle that is an acute angle of 60 degrees or less.

6. The process of claim 1 wherein the article has a tensile strength at yield of greater than 5,000 psi, and a flex modulus at 100° C. greater than 1,000 psi.

7. The process of claim 1 wherein the thermoplastic polymer is a combination of a thermoplastic polymer with a flame retardant compound.

8. The process of claim 7 wherein the flame retardant compound is chosen from a brominated thermoplastic resin, a non-brominated phosphate compound, a phosphinate salt, C1-16 sulfonate salt, or a combination thereof.

9. The process of claim 8 wherein the flame retardant compound is a brominated thermoplastic resin.

10. The process of claim 8 wherein the flame retardant compound is a non-brominated phosphate compound.

11. The process of claim 1 wherein the thermoplastic polymer is an amorphous thermoplastic polycarbonate, acrylonitrile butadiene styrene (ABS), polyetherimide (PEI), polyethersulfone (PES), polysulfone (PSu), polyphenylene oxide (PPO), polyphenylene ether (PPE), polyphenylene ether sulfone (PPSU), styrene-acrylonitrile (SAN), or silicone polycarbonate copolymers, or any combination thereof.

12. The process of claim 1 wherein the thermoplastic polymer is a thermoplastic polycarbonate.

13. The process claim 1 wherein the thermoplastic polymer is a polycarbonate blended with acrylonitrile butadiene styrene (ABS), polyetherimide (PEI), styrene-acrylonitrile (SAN), polytetrafluoroethylene (PTFE) polybutylene terephthalate (PBT), polyethylene terephthalate (PET), or phenyl cyclohexyl dimethanol terephthalate (PCT), or combinations thereof.

14. The process claim 1 wherein the thermoplastic polymer is a thermoplastic resin having flame resistant properties.

15. The process of claim 1 wherein the thermoplastic polymer composition further comprises a metal synergist.

16. A reduced density flame resistant article of manufacture made by the process of claim 1 wherein at least 90% of the voids are high aspect voids and less than 10% of the voids are spherical voids with a diameter of 10 to 100 microns.

* * * * *